United States Patent
Schomacker et al.

(10) Patent No.: US 7,103,401 B2
(45) Date of Patent: Sep. 5, 2006

(54) COLONIC POLYP DISCRIMINATION BY TISSUE FLUORESCENCE AND FIBEROPTIC PROBE

(75) Inventors: Kevin T. Schomacker, Maynard, MA (US); Norman S. Nishioka, Wayland, MA (US); Alex R. Zelenchuk, Stoughton, MA (US)

(73) Assignee: MediSpectra, Inc., Lexington, MA (US)

( * ) Notice: Subject to any disclaimer, the term of this patent is extended or adjusted under 35 U.S.C. 154(b) by 380 days.

(21) Appl. No.: 10/192,820

(22) Filed: Jul. 10, 2002

(65) Prior Publication Data
US 2004/0010187 A1 Jan. 15, 2004

(51) Int. Cl.
*A61B 6/00* (2006.01)

(52) U.S. Cl. .............. 600/476; 600/407; 600/473; 600/101; 600/108; 356/456; 351/212; 351/206; 351/227; 351/246

(58) Field of Classification Search ............ 600/473, 600/476, 101, 108; 356/345, 346, 456; 307/211, 307/206, 221, 246
See application file for complete search history.

(56) References Cited

U.S. PATENT DOCUMENTS

| | | | |
|---|---|---|---|
| 3,013,467 A | 12/1961 | Minsky | 88/14 |
| 3,632,865 A | 1/1972 | Haskell et al. | 178/6 |
| 3,809,072 A | 5/1974 | Ersek et al. | 128/23 |
| 3,890,462 A | 6/1975 | Limb et al. | 178/6.8 |
| 3,963,019 A | 6/1976 | Quandt et al. | 128/2 |
| D242,393 S * | 11/1976 | Bauman | |

(Continued)

FOREIGN PATENT DOCUMENTS

| | | |
|---|---|---|
| EP | 0 135 134 | 3/1985 |
| EP | 0 280 418 | 8/1988 |

(Continued)

OTHER PUBLICATIONS

Agrawal et al. (1999), "Fluorescence Spectroscopy of the Cervix: Influence of Acetic Acid, Cervical Mucus, and Vaginal Medications," *Lasers in Surgery and Medicine*, 25:237–249.

Althof et al. (1997), "A rapid and automatic image registration algorithm with subpixel accuracy," *IEEE Transactions on Medical Imaging*, 16(3):308–316.

Anderson (1994), "Confocal Laser Microscopes See A Wider Field of Application", *Laser Focus World*, pp. 83–86.

Aström et al. (1999), "Motion estimation in image sequences using the deformation of apparent contours," *IEEE Transactions on Pattern Analysis and Machine Intelligence*, 21(2):114–127.

(Continued)

*Primary Examiner*—Max F. Hindenburg
*Assistant Examiner*—William C. Jung
(74) *Attorney, Agent, or Firm*—Testa Hurwitz & Thibeault, LLP

(57) ABSTRACT

A system and method for the in situ discrimination of healthy and diseased tissue. A fiberoptic based probe is employed to direct ultraviolet illumination onto a tissue specimen and to collect the fluorescent response radiation. The response radiation is observed at three selected wavelengths, about 403 nm, about 414 nm, and about 431 nm. The intensities of the 403 nm and 414 mn radiation are normalized using the 431 nm intensity. A score is determined using the ratios in a linear discriminant analysis (LDA). The tissue under examination is resected or not, based on the outcome of the LDA.

10 Claims, 4 Drawing Sheets

U.S. PATENT DOCUMENTS

| | | | |
|---|---|---|---|
| D242,396 S | * 11/1976 | Bauman | |
| D242,397 S | * 11/1976 | Bauman | |
| D242,398 S | * 11/1976 | Bauman | |
| 4,017,192 A | 4/1977 | Rosenthal et al. | 356/201 |
| 4,071,020 A | 1/1978 | Puglise et al. | 128/2 |
| 4,198,571 A | 4/1980 | Sheppard | 250/571 |
| 4,218,703 A | 8/1980 | Netravali et al. | 358/136 |
| 4,254,421 A | 3/1981 | Kreutel, Jr. | 343/754 |
| 4,273,110 A | 6/1981 | Groux | 128/6 |
| 4,357,075 A | 11/1982 | Hunter | 350/294 |
| 4,397,557 A | 8/1983 | Herwig et al. | 356/342 |
| 4,549,229 A | 10/1985 | Nakano et al. | 360/8 |
| 4,646,722 A | * 3/1987 | Silverstein et al. | 128/4 |
| 4,662,360 A | 5/1987 | O'Hara et al. | 128/9 |
| 4,733,063 A | 3/1988 | Kimura et al. | 250/201 |
| 4,741,326 A | 5/1988 | Sidall et al. | 128/4 |
| 4,753,530 A | 6/1988 | Knight et al. | 356/73 |
| 4,768,513 A | 9/1988 | Suzuki | 128/634 |
| 4,800,571 A | 1/1989 | Konishi | 375/10 |
| 4,844,617 A | 7/1989 | Kelderman et al. | 356/372 |
| 4,845,352 A | 7/1989 | Benschop | 250/201 |
| 4,852,955 A | 8/1989 | Doyle et al. | 350/1.2 |
| 4,877,033 A | 10/1989 | Seitz, Jr. | 128/660.05 |
| 4,878,485 A | 11/1989 | Adair | 128/6 |
| 4,891,829 A | 1/1990 | Deckman et al. | 378/4 |
| 4,930,516 A | 6/1990 | Alfano et al. | 128/665 |
| 4,945,478 A | 7/1990 | Merickel et al. | 364/413.22 |
| 4,965,441 A | 10/1990 | Picard | 250/201.3 |
| 4,972,258 A | 11/1990 | Wolf et al. | 358/93 |
| 4,974,580 A | 12/1990 | Anapliotis | 128/4 |
| 4,979,498 A | 12/1990 | Oneda et al. | 128/6 |
| 4,997,242 A | 3/1991 | Amos | 350/6.91 |
| 5,003,979 A | 4/1991 | Merickel et al. | 364/413.22 |
| 5,011,243 A | 4/1991 | Doyle et al. | 350/1.2 |
| 5,022,757 A | 6/1991 | Modell | 356/318 |
| 5,028,802 A | 7/1991 | Webb et al. | 250/571 |
| 5,032,720 A | 7/1991 | White | 250/236 |
| 5,034,613 A | 7/1991 | Denk et al. | 250/458.1 |
| 5,036,853 A | 8/1991 | Jeffcoat et al. | 128/634 |
| 5,042,494 A | 8/1991 | Alfano | 128/665 |
| 5,048,946 A | 9/1991 | Sklar et al. | 351/206 |
| 5,054,926 A | 10/1991 | Dabbs et al. | 356/345 |
| 5,065,008 A | 11/1991 | Hakamata et al. | 250/216 |
| 5,071,246 A | 12/1991 | Blaha et al. | 351/221 |
| 5,074,306 A | 12/1991 | Green et al. | 128/664 |
| 5,083,220 A | 1/1992 | Hill | 359/234 |
| 5,091,652 A | 2/1992 | Mathies et al. | 250/458.1 |
| 5,101,825 A | * 4/1992 | Gravenstein et al. | 128/633 |
| 5,120,953 A | 6/1992 | Harris | 250/227.2 |
| 5,122,653 A | 6/1992 | Ohki | 250/216 |
| 5,132,526 A | 7/1992 | Iwasaki | 250/201.3 |
| 5,139,025 A | 8/1992 | Lewis et al. | 128/665 |
| 5,154,166 A | 10/1992 | Chikama | 128/4 |
| 5,159,919 A | 11/1992 | Chikama | 128/4 |
| 5,161,053 A | 11/1992 | Dabbs | 359/384 |
| 5,162,641 A | 11/1992 | Fountain | 250/201.2 |
| 5,162,941 A | 11/1992 | Favro et al. | 359/386 |
| 5,168,157 A | 12/1992 | Kimura | 250/234 |
| 5,192,980 A | 3/1993 | Dixon et al. | 356/326 |
| 5,193,525 A | * 3/1993 | Silverstein et al. | 128/4 |
| RE34,214 E | 4/1993 | Carlsson et al. | 358/93 |
| 5,199,431 A | 4/1993 | Kittrell et al. | 128/634 |
| 5,201,318 A | 4/1993 | Rava et al. | 128/665 |
| 5,201,908 A | 4/1993 | Jones | 128/4 |
| 5,203,328 A | 4/1993 | Samuels et al. | 128/633 |
| 5,225,671 A | 7/1993 | Fukuyama | 250/216 |
| 5,235,457 A | 8/1993 | Lichtman et al. | 359/368 |
| 5,237,984 A | 8/1993 | Williams, III et al. | 128/4 |
| 5,239,178 A | 8/1993 | Derndinger et al. | 250/234 |
| 5,248,876 A | 9/1993 | Kerstens et al. | 250/561 |
| 5,253,071 A | 10/1993 | MacKay | 358/222 |
| 5,257,617 A | 11/1993 | Takahashi | 128/4 |
| 5,260,569 A | 11/1993 | Kimura | 250/234 |
| 5,260,578 A | 11/1993 | Bliton et al. | 250/461.1 |
| 5,261,410 A | 11/1993 | Alfano et al. | 128/664 |
| 5,262,646 A | 11/1993 | Booker et al. | 250/341 |
| 5,274,240 A | 12/1993 | Mathies et al. | 250/458.1 |
| 5,284,149 A | 2/1994 | Dhadwal et al. | 128/665 |
| 5,286,964 A | 2/1994 | Fountain | 250/201.2 |
| 5,289,274 A | 2/1994 | Kondo | 348/208 |
| 5,294,799 A | 3/1994 | Aslund et al. | 250/458.1 |
| 5,296,700 A | 3/1994 | Kumagai | 250/216 |
| 5,303,026 A | 4/1994 | Strobl et al. | 356/318 |
| 5,306,902 A | 4/1994 | Goodman | 250/201.3 |
| 5,313,567 A | 5/1994 | Civanlar et al. | 395/124 |
| 5,319,200 A | 6/1994 | Rosenthal et al. | 250/341 |
| 5,321,501 A | 6/1994 | Swanson et al. | 356/345 |
| 5,324,979 A | 6/1994 | Rosenthal | 250/504 R |
| 5,325,846 A | 7/1994 | Szabo | 128/4 |
| 5,329,352 A | 7/1994 | Jacobsen | 356/301 |
| 5,337,734 A | 8/1994 | Saab | 128/4 |
| 5,343,038 A | 8/1994 | Nishiwaki et al. | 250/234 |
| 5,345,306 A | 9/1994 | Ichimura et al. | 356/346 |
| 5,345,941 A | 9/1994 | Rava et al. | 128/665 |
| 5,349,961 A | 9/1994 | Stoddart et al. | 128/665 |
| 5,398,685 A | 3/1995 | Wilk et al. | 128/653.1 |
| 5,402,768 A | 4/1995 | Adair | 128/4 |
| 5,406,939 A | 4/1995 | Bala | 128/4 |
| 5,413,092 A | 5/1995 | Williams, III et al. | 128/4 |
| 5,413,108 A | 5/1995 | Alfano | 128/665 |
| 5,415,157 A | 5/1995 | Welcome | 128/4 |
| 5,418,797 A | 5/1995 | Bashkansky et al. | 372/3 |
| 5,419,311 A | 5/1995 | Yabe et al. | 128/4 |
| 5,419,323 A | 5/1995 | Kittrell et al. | 128/653 |
| 5,421,337 A | 6/1995 | Richards-Kortum et al. | 128/665 |
| 5,421,339 A | 6/1995 | Ramanujam et al. | 128/665 |
| 5,424,543 A | 6/1995 | Dombrowski et al. | 250/330 |
| 5,450,857 A | 9/1995 | Garfield et al. | 128/778 |
| 5,451,931 A | 9/1995 | Miller et al. | 340/630 |
| 5,458,132 A | 10/1995 | Yabe et al. | 128/4 |
| 5,458,133 A | 10/1995 | Yabe et al. | 600/121 |
| 5,467,767 A | 11/1995 | Alfano et al. | 128/665 |
| 5,469,853 A | * 11/1995 | Law et al. | 128/662.06 |
| 5,477,382 A | 12/1995 | Pernick | 359/559 |
| 5,480,775 A | 1/1996 | Ito et al. | 435/7.2 |
| 5,493,444 A | 2/1996 | Khoury et al. | 359/559 |
| 5,496,259 A | * 3/1996 | Perkins | 600/124 |
| 5,507,295 A | 4/1996 | Skidmore | 600/121 |
| 5,516,010 A | 5/1996 | O'Hara et al. | 600/122 |
| 5,519,545 A | 5/1996 | Kawahara | 360/46 |
| 5,529,235 A | 6/1996 | Boiarski et al. | 227/175.1 |
| 5,536,236 A | 7/1996 | Yabe et al. | 600/125 |
| 5,545,121 A | 8/1996 | Yabe et al. | 600/121 |
| 5,551,945 A | 9/1996 | Yabe et al. | 600/121 |
| 5,556,367 A | 9/1996 | Yabe et al. | 600/124 |
| 5,562,100 A | 10/1996 | Kittrell et al. | 128/665 |
| 5,579,773 A | 12/1996 | Vo-Dinh et al. | 128/665 |
| 5,582,168 A | 12/1996 | Samuels et al. | 128/633 |
| 5,587,832 A | 12/1996 | Krause | 359/385 |
| 5,596,992 A | 1/1997 | Haaland et al. | 128/664 |
| 5,599,717 A | 2/1997 | Vo-Dinh | 436/63 |
| 5,609,560 A | 3/1997 | Ichikawa et al. | 600/101 |
| 5,612,540 A | 3/1997 | Richards-Korum et al. | 250/461.2 |
| 5,623,932 A | 4/1997 | Ramanujam et al. | 128/665 |
| 5,647,368 A | 7/1997 | Zeng et al. | 128/665 |
| 5,662,588 A | 9/1997 | Lida | 600/121 |
| 5,685,822 A | 11/1997 | Harhen | 600/125 |
| 5,690,106 A | 11/1997 | Bani-Hashemi et al. | 128/653.1 |
| 5,693,043 A | 12/1997 | Kittrell et al. | 606/15 |

| | | | |
|---|---|---|---|
| 5,695,448 A | 12/1997 | Kimura et al. | 600/121 |
| 5,697,373 A | 12/1997 | Richards-Kortum et al. | 128/664 |
| 5,699,795 A | 12/1997 | Richards-Kortum | 128/634 |
| 5,704,892 A | 1/1998 | Adair | 600/121 |
| 5,707,343 A | 1/1998 | O'Hara et al. | 600/121 |
| 5,713,364 A | 2/1998 | DeBaryshe et al. | 128/664 |
| 5,717,209 A | 2/1998 | Bigman et al. | 250/339.12 |
| 5,730,701 A | 3/1998 | Furukawa et al. | 600/127 |
| 5,733,244 A | 3/1998 | Yasui et al. | 600/127 |
| 5,735,276 A * | 4/1998 | Lemelson | 128/653.1 |
| 5,746,695 A | 5/1998 | Yasui et al. | 600/127 |
| 5,768,333 A | 6/1998 | Abdel-Mottaleb | 378/37 |
| 5,769,792 A | 6/1998 | Palcic et al. | 600/477 |
| 5,773,835 A | 6/1998 | Sinofsky et al. | 250/462.1 |
| 5,791,346 A | 8/1998 | Craine et al. | 128/653 |
| 5,795,632 A | 8/1998 | Buchalter | 428/35.2 |
| 5,800,350 A | 9/1998 | Coppleson et al. | 600/372 |
| 5,807,248 A | 9/1998 | Mills | 600/322 |
| 5,813,987 A | 9/1998 | Modell et al. | 600/473 |
| 5,817,015 A | 10/1998 | Adair | 600/121 |
| 5,830,146 A * | 11/1998 | Skladnev et al. | 600/478 |
| 5,833,617 A | 11/1998 | Hayashi | 600/476 |
| 5,840,035 A | 11/1998 | Heusmann et al. | 600/47 |
| 5,842,995 A | 12/1998 | Mahadevan-Jansen et al. | 600/473 |
| 5,855,551 A | 1/1999 | Sklandnev et al. | 600/372 |
| 5,860,913 A | 1/1999 | Yamaya et al. | 600/127 |
| 5,863,287 A * | 1/1999 | Segawa | 600/121 |
| 5,865,726 A | 2/1999 | Katsurada et al. | 600/127 |
| 5,876,329 A | 3/1999 | Harhen | 600/125 |
| 5,920,399 A | 7/1999 | Sandison et al. | 356/418 |
| 5,921,926 A | 7/1999 | Rolland et al. | 600/407 |
| 5,929,985 A | 7/1999 | Sandison et al. | 365/318 |
| 5,931,779 A | 8/1999 | Arakaki et al. | 600/310 |
| 5,938,617 A | 8/1999 | Vo-Dinh | 600/476 |
| 5,941,834 A * | 8/1999 | Skladnev et al. | 600/587 |
| 5,983,125 A * | 11/1999 | Alfano et al. | 600/473 |
| 5,989,184 A | 11/1999 | Blair et al. | 600/167 |
| 5,991,653 A | 11/1999 | Richards-Kortum et al. | 660/475 |
| 5,995,645 A | 11/1999 | Soenksen et al. | 382/133 |
| 6,021,344 A * | 2/2000 | Lui et al. | 600/476 |
| 6,058,322 A | 5/2000 | Nishikawa et al. | 600/408 |
| 6,069,689 A | 5/2000 | Zeng et al. | 356/773 |
| 6,091,985 A * | 7/2000 | Alfano et al. | 600/476 |
| 6,095,982 A * | 8/2000 | Richards-Kortum et al. | 600/476 |
| 6,096,065 A * | 8/2000 | Crowley | 607/88 |
| 6,099,464 A * | 8/2000 | Shimizu et al. | 600/104 |
| 6,104,945 A | 8/2000 | Modell et al. | 600/473 |
| 6,119,031 A | 9/2000 | Crowley | 600/407 |
| 6,124,597 A * | 9/2000 | Shehada et al. | 250/461.2 |
| 6,146,897 A | 11/2000 | Cohenford et al. | 436/63 |
| 6,169,817 B1 | 1/2001 | Parker et al. | 382/131 |
| 6,208,887 B1 | 3/2001 | Clarke et al. | 600/476 |
| 6,241,662 B1 | 6/2001 | Richards-Kortum et al. | 600/310 |
| 6,243,601 B1 * | 6/2001 | Wist | 600/473 |
| 6,246,471 B1 | 6/2001 | Jung et al. | 356/73 |
| 6,246,479 B1 | 6/2001 | Jung et al. | 356/419 |
| 6,285,639 B1 | 9/2001 | Maenza et al. | 369/47.28 |
| 6,312,385 B1 | 11/2001 | Mo et al. | 600/443 |
| 6,317,617 B1 | 11/2001 | Gilhijs et al. | 600/408 |
| D453,832 S * | 2/2002 | Morrell et al. | D24/138 |
| D453,962 S * | 2/2002 | Morrell et al. | D24/138 |
| D453,963 S * | 2/2002 | Morrell et al. | D24/138 |
| D453,964 S * | 2/2002 | Morrell et al. | D24/138 |
| 6,377,842 B1 | 4/2002 | Pogue et al. | 600/478 |
| 6,385,484 B1 | 5/2002 | Nordstrom et al. | 600/476 |
| 6,411,835 B1 * | 6/2002 | Modell et al. | 600/407 |
| 6,411,838 B1 | 6/2002 | Nordstrom et al. | 600/476 |
| D460,821 S * | 7/2002 | Morrell et al. | D24/138 |
| 6,421,553 B1 | 7/2002 | Costa et al. | 600/476 |
| 6,427,082 B1 | 7/2002 | Nordstrom et al. | 600/476 |
| 6,571,118 B1 * | 5/2003 | Utzinger et al. | 600/476 |
| 6,574,502 B1 * | 6/2003 | Hayashi | 600/476 |
| 2002/0007123 A1 | 1/2002 | Balas et al. | 600/476 |

FOREIGN PATENT DOCUMENTS

| | | |
|---|---|---|
| EP | 0 335 725 | 10/1989 |
| EP | 0 444 689 A2 | 9/1991 |
| EP | 0 474 264 | 3/1992 |
| EP | 0 641 542 | 3/1995 |
| EP | 0 689 045 A1 | 12/1995 |
| EP | 0 737 849 A2 | 10/1996 |
| JP | 08-280602 | 10/1996 |
| SU | 1 223 092 A | 4/1986 |
| WO | WO 92/19148 | 11/1992 |
| WO | WO 93/14688 | 8/1993 |
| WO | WO 94/26168 | 11/1994 |
| WO | 95/00067 | 1/1995 |
| WO | WO 95/04385 | 2/1995 |
| WO | WO 97/05473 | 2/1997 |
| WO | WO 98/30889 | 2/1997 |
| WO | WO 97/48331 | 12/1997 |
| WO | WO 98/05253 | 2/1998 |
| WO | WO 98/24369 | 6/1998 |
| WO | WO 98/41176 | 9/1998 |
| WO | WO 99/18847 | 4/1999 |
| WO | WO 99/20313 | 4/1999 |
| WO | WO 99/20314 | 4/1999 |
| WO | WO 99/47041 | 9/1999 |
| WO | WO 99/57507 | 11/1999 |
| WO | WO 99/57529 | 11/1999 |
| WO | WO 00/15101 | 3/2000 |
| WO | WO 00/59366 | 10/2000 |

OTHER PUBLICATIONS

Balakrishnama et al, "Linear Discriminant Analysis—A Brief Tutorial," *Institute for Signal and Information Processing Department of Electrical and Computer Engineering*, 8 pages.

Balas (1997), "An Imaging Colorimeter for Noncontact Tissue Color Mapping," *IEEE Transactions on Biomedical Engineering*, 44(6):468–474.

Balas (2001), "A Novel Optical Imaging Method for the Early Detection, Quantitative Grading, and Mapping of Cancerous and Precancerous Lesions of Cervix," *IEEE Transactions on Biomedical Engineering*, 48(1):96–104.

Balas et al. (1997), "A modular diffuse reflection and fluorescence emission imaging colorimeter for the in–vivo study of parameters related with the phototoxic effect in PDT," *SPIE*, 3191:50–57.

Balas et al. (1998), "In Vivo Assessment of Acetic Acid–Cervical Tissue Interaction Using Quantitative Imaging of Back–Scattered Light: Its Potential Use for the In Vivo Cervical Cancer Detection Grading and Mapping," Part of EUROPTO Conference on Optical Biopsy, Stockholm, Sweden, *SPIE*, vol. 3568:31–37.

Balas et al. (1999), "In Vivo Detection and Staging of Epithelial Dysplasias and Malignancies Based on the Quantitative Assessment of Acetic Acid–Tissue Interaction Kinetics," *Journal of Photochemistry and Photobiology B: Biology*, 53:153–157.

Bessey et al. (1949), "The Fluorometric measurement of the nucleotides of riboflavin and their concentration in tissues," *J. Biol.–Chem.*; 180:755–769.

Bors et al. (1998), "Optical flow estimation and moving object segmentation based on median radial basis function network," *IEEE Transactions on Image Processing*, 7(5):693–702.

Bouthemy et al. (1999), "A unified approach to shot change detection and camera motion characterization," *IEEE Transactions on Circuits and Systems for Video–Technology*, 9(7):1030–1044.

Braichotte et al. (1995), "Clinical Pharmacokinetic Studies of Photofrin by Fluorescence Spectroscopy in the Oral Cavity, the Esophagus, and the Bronchi," *Cancer* 75(11):2760–2778.

Brown (1990), "Chemometrics," *Anal. Chem.*, 62:84R–101R.

Camus et al. (1997), "Real–time quantized optical flow," *Real–Time Imaging*, 3:71–86.

Caplier et al. (1998), "Real–time implementation of a MRF–based motion detection algorithm," *Real–Time Imaging*, 4:41–54.

Contini et al. (1989), "Colposcopy and Computer Graphics: a New Method?" *Amer. J. Obstet. Gynecol.*, 160(3):535–538.

Craine et al. (1993), "Digital Imaging Colposcopy: basic concepts and applications," *Amer. J. Obstet. Gynecol.*, 82(5):869–873.

Craine et al. (1998), "Digital imaging colposcopy: Corrected area measurements using shape–from–shading," *IEEE Transactions on Medical Imaging*, 17(6):1003–1010.

Crisp et al. (1990), "The Computerized Digital Imaging Colposcope: Future Directions," *Amer. J. Obstet. Gynecol.*, 162(6):1491–1497.

Cronjé et al. (1997), "Effects of Dilute Acetic Acid on the Cervical Smear," *Acta. Cytol.*, 41:1091–1094.

Davidovits et al. (1971), "Scanning Laser Microscope for Biological Investigations", *Applied Optics*, 10(7):1615–1619.

Dickman et al. (2001), "Identification of Cervical Neoplasia Using a Simulation of Human Vision," *Journal of Lower Genital Tract Disease*, 5(3):144–152.

Drezek et al. (1999), "Light scattering from cells: finite–difference time–domain simulations and goniometric measurements," *Applied Optics* 38(16):3651–3661.

Drezek et al. (2000), "Laser Scanning Confocal Microscopy of Cervical Tissue Before and After Application of Acetic Acid," *Am. J. Obstet. Gynecol.*, 182(5):1135–1139.

Dumontier et al. (1999), "Real–time DSP implementation for MRF–based video motion detection," *IEEE Transactions on Image Processing*, 8(10):1341–1347.

Earnshaw et al. (1996), "The Performance of Camera Translation Direction Estimators from Optical Flow: Analysis, Comparison, and Theoretical Limits," *IEEE Transactions on Pattern Analysis and Machine Intelligence*, 18(9):927–932.

Edebiri, A.A. (1990), "The relative significance of colposcopic discriptive appearances in the dianosis of cervical intraepithelial neoplasia," *Int. J. Gynecol. Obstet.*, 33:23–29.

Eisner et al. (1987), "Use of Cross–Correlation Function to Detect Patient Motion During Spectral Imaging," *Journal of Nuclear Medicine*, 28(1):97–101.

Ferris et al. (1998), "Colposcopy Quality Control: Establishing Colposcopy Criterion Standards for the NCI ALTS Trial Using Cervigrams," *J. Lower Genital Tract Disease*, 2(4):195–203.

Fleet et al. (1995), "Recursive Filters for Optical Flow," *IEEE Transactions on Pattern Analysis and Machine Intelligence*, 17(1):61–67.

Gao et al. (1998), "A work minimization approach to image morphing," *The Visual Computer*, 14:390–400.

Gauch (1999), "Image Segmentation and Analysis Via Multiscale Gradient Watershed Hierarchies," *IEEE Transactions on Image Processing*, 8(1):69–79.

Hall et al. (1992), "Near–Infrared Spectrophotometry: A New Dimension in Clinical Chemistry", *Clin. Chem.* 38(9):1623–1631.

Haralick (1984), "Digital Step Edges from Zero Crossing of Second Directional Derivatives," *IEEE Transactions on Pattern Analysis and Machine Intelligence*, 6(1):58–68.

Haris et al. (1998), "Hybrid Image Segmentation Using Watersheds and Fast Region Merging," *IEEE Transactions on Image Processing*, 7(12):1684–1699.

Helmerhorst et al. (1987), "The accuracy of colposcopically directed biopsy in diagnosis of CIN 2/3." *Eur. J. Obstet. Gyn. Reprod. Biol.*, 24, 221–229.

Horn et al. (1981), "Determining Optical Flow," *Artificial Intelligence*, 17(1–3):185–203.

Horn et al. (1993), "Determining Optical Flow": a retrospective, *Artificial Intelligence*, 59:81–87.

Huang et al. (1979), "A fast two–dimensional median filtering algorithm," *IEEE Transactions on Acoustics, Speech, and Signal Processing*, 27(1):13–18.

Jackway (1996), "Gradient Watersheds in Morphological Scale–Space," *IEEE Transactions on Image Processing*, 5(6):913–921.

Ji et al. (2000), "Texture Analysis for Classification of Cervix Lesions," *IEEE Transactions on Medical Imaging*, 19(11):1144–1149.

Kierkegaard et al. (1995), "Association between Colposcopic Findings and Histology in Cervical Lesions: The Significance of the Size of the Lesion" *Gynecologic Oncology*, 57:66–71.

Koester (1980), "Scanning Mirror Microscope with Optical Sectioning Characteristics: Applications in Ophthalmology", *Applied Optics*, 19(11):1749–1757.

Koester, "Comparison of Optical Sectioning Methods: The Scanning Slit Confocal Microscope", *Confocal Microscope Handbook*, pp. 189–194.

Kumar et al. (1996), "Optical Flow: A Curve Evolution Approach," *IEEE Transactions on Image Processing*, 5(4):598–610.

Linde et al. (1980), An algorithm for vector quantizer design,: *IEEE Transactions on Communications*, 28(1):84–95.

MacAulay et al. (2002), "Variation of fluorescence spectroscopy during the menstrual cycle," *Optics Express*, 10(12):493–504.

MacLean A.B. (1999), "What is Acetowhite Epithelium," *Abstract Book*; 10th *World Congress of Cervical Pathology and Colposcopy*, Nov. 7–11, Buenos Aires, Argentina 41.

Marzetta et al. (1999), "A surprising radon transform result and its application to motion detection," *IEEE Transactions on Image Processing*, 8(8):1039–1049.

Miike et al. (1999), "Motion enhancement for preprocessing of optical flow and scientific visualization," *Pattern Recognition Letters*, 20:451–461.

Mikhail et al. (1995), "Computerized colposcopy and conservative management of cervical intraepithelial neoplasia in pregnancy," *Acta Obstet. Gynecol. Scand.*, 74:376–378.

Milanfar (1999), "Two-dimensional matched filtering for motion estimation," *IEEE Transactions on Image Processing*, 8(3):438–444.

Mitchell et al. (1998), "Colposcopy for the diagnosis of squamous intraepithelial lesions: a meta-analysis," *Obstet. Gynecol.*, 91(4):626–631.

Mycek et al. (1998), "Colonic polyp differentiation using time-resolved autofluorescence spectroscopy," *Gastrointestinal Endoscopy*, 48(4):390–394.

Nanda et al. (2000), "Accuracy of the Papanicolaou test in screening for and follow-up of cervical cytologic abnormalities: a systematic review," *Ann Intern Med.*, 132(10):810–819.

Nesi et al. (1998), "RETIMAC REalTIme Motion Analysis Chip," *IEEE Transactions on Circuits and Systems–II: Analog and Digital Signal Processing*, 45(3):361–375.

Noumeir et al. (1996), "Detection of Motion During Tomographic Acquisition by an Optical Flow Algorithm," *Computers and Biomedical Research*, 29(1):1–15.

O'Sullivan et al. (1994), "Interobserver variation in the diagnosis and grading of dyskaryosis in cervical smears: specialist cytopathologists compared with non-specialists," *J. Clin. Pathol.*, 47(6):515–518.

Ogura et al. (1995), "A cost effective motion estimation processor LSI using a simple and efficient algorithm," *IEEE Transactions on Consumer Electronics*, 41(3):690–698.

Okatani et al. (1997), "Shape reconstruction from an endoscope image by shape from shading technique for a point light source at the projection center," *Computer Vision and Image Understanding*, 66(2):119–131.

Pan et al. (1998), "Correlation-feedback Technique in Optical Flow Determination," *IEEE Transactions on Image Processing*, 7(7):1061–1067.

Perona et al. (1990), "Scale-space and edge detection using anisotropic diffusion," *IEEE Transactions on Pattern Analysis and Machine Intelligence*, 12(7):629–639.

Pogue et al. (2001), "Analysis of Acetic Acid-Induced Whitening of High-Grade Squamous Intraepithelial Lesions," *Journal of Biomedical Optics*, 6(4):397–403.

Radjadhyaksha et al. (2000), "Confocal microscopy of excised human skin using acetic acid and crossed polarization: rapid detection of non-melanoma skin cancers," *Proceedings of SPIE*, 3907:84–88.

Rakshit et al. (1997), "Computation of Optical Flow Using Basis Functions," *IEEE Transactions on Image Processing*, 6(9):1246–1254.

Ramanujam et al. (1994) "In vivo diagnosis of cervical intraepithelial neoplasia using 337–nm–exited laser-induced fluorescence", *Pro. Natl. Acad. Sci. USA*, 91:10193–10197.

Ramanujam et al. (1994), "Fluorescence Spectroscopy; A Diagnostic Tool for Cervical Intraepithelial Neoplasia (CIN)," *Gynecologic Oncology*, 52:31–38.

Reid et al. (1985), "Genital warts and cervical cancer. VII. An improved colposcopic index for differentiating benign papillomaviral infections from high–grade CIN," *Am. J. Obstet. Gynecol.*, 153(6):611–618.

Richards–Korrum et al. (1994), "Description and Performance of a Fiber-optic Confocal Fluorescence Spectrometer," *Applied Spectroscopy*, 48(3):350–355.

Romano et al. (1997), "Spectroscopic study of human leukocytes," *Physica Medica*, 13:291–295.

Ruprecht et al. (1995), "Image warping with scattered data interpolation methods," *IEEE Computer Graphics and Applications*, 37–43.

Sakuma (1985), "Quantitative Analysis of the Whiteness of the Atypical Cervical Transformation Zone", *The Journal of Reproductive Medicine*, 30(10):773–776.

Schmid (1999), "Lesion Detection in Dermatoscopic Images Using Anisotropic Diffusion and Morphological Flooding," *Proceedings of the International Conference on Image Processing (ICIP–99)*, 3:449–453.

Schmid (1999), "Segmentation and Symmetry Measure for Image Analysis: Application to Digital Dermatoscopy," *Ph.D. Thesis. Swiss Federal Institute of Technology (EPFL), Signal Processing Laboratory(LTS)*.

Schmid (1999), "Segmentation of Digitized Dermatoscopic Images by 2D Color Clustering," *IEEE Transactions on Medical Imaging*, 18(2):164–171.

Schmitt et al. (1994), "Confocal Microscopy in Turbid Media", *J. Opt. Soc. Am. A*, 11(8):2225–2235.

Schmitt et al. (1994), "Interferometric Versus Confocal Techniques for Imaging Microstructures in Turbid Biological Media", *Proc. SPIE*, 2135:1–12.

Schomacker et al. (1992), "Ultraviolet Laser-Induced Fluorescence of Colonic Polyps," *Gastroenterology*, 102:1155–1160.

Schomacker et al. (1992), "Ultraviolet Laser-Induced Fluorescence of Colonic Tissue; Basic Biology and Diagnostic Potential", *Lasers in Surgery and Medicine*, 12:63–78.

Schwartz (1993), "Real-time laser-scanning Confocal ratio imaging", *American Laboratory*, pp. 53–62.

Shafarenko et al. (1997), "Automatic Watershed Segmentation of Randomly Textured Color Images," *IEEE Transactions on Image Processing*, 6(11):1530–1544.

Shafi et al. (1995), "Modern image capture and data collection technology," *Clin. Obstet. Gynecol.*, 38(3):640–643.

Sheppard et al. (1978), "Depth of Field in the Scanning Microscope", *Optics Letters*, 3(3):115–117.

Szarewski et al., (1996), "Effect of smoking cessation on cervical lesions size," *Lancet*, 347:941–943.

Szeliski et al. (1997), "Spline–based image registration," *International Journal of Computer Vision*, 22(3):199–218.

Tadrous (2000), "Methods for Imaging the Structure and Function of Living Tissues and Cells: 2. Fluorescence Lifetime Imaging," *Journal of Pathology*, 191(3):229–234.

Thirion et al. (1999), "Deformation analysis to detect and quantify active lesions in three-dimensional medical image sequences," *IEEE Transactions on Medial Imaging*, 18(5):429–441.

Toglia et al. (1997), "Evaluation of colposcopic skills in an obstetrics and gynecology residency training program," *J. Lower Gen. Tract. Dis.*, 1(1):5–8.

Treameau et al. (1997), "A Region Growing and Merging Algorithm to Color Segmentation," *Pattern Recognition*, 30(7):1191–1203.

Van den Elsen et al. (1995), "Automatic registration of ct and mr brain images using correlation of geometrical features," *IEEE Transactions on medical imaging*, 14(2):384–396.

Vernon (1999), "Computation of Instantaneous Optical Flow Using the Phase of Fourier Components," *Image and Vision Computing*, 17:189–199.

Vincent et al. (1991), "Watersheds in Digital Spaces: An Efficient Algorithm Based on Immersion Simulations," *IEEE Transactions on Patterns Analysis and Machine Intelligence*, 13(6):583–598.

Vincent et al. (1993), "Morphological grayscale reconstruction in image analysis: Applications and efficient algorithms," *IEEE Transactions on Image Processing*, 2(2):176–201.

Wang et al. (1999), "Fast algorithms for the estimation of motion vectors," *IEEE Transactions on Image Processing*, 8(3):435–438.

Weng et al. (1997), "Three–Dimensional Surface Reconstruction Using Optical Flow for Medical Imaging," *IEEE Transactions on Medical Imaging*, 16(5):630–641.

Wilson, "The Role of the Pinhold in Confocal Imaging Systems", *Confocal Microscopy Handbook*, Chapter 11, 113–126.

Wolberg et al. (1998) "Image morphing: a survey," *The Visual Computer*, 14:360–372.

You et al. (1996), "Behavioral analysis of anisotropic diffusion in image processing," *IEEE Transactions on Image Processing*, 5(11):1539–1553.

Zahm et al. (1998), "Colposcopic appearance of cervical intraepithelial neoplasia is age dependent," *Am. J. Obstet. Gynecol.*, 179(5):1298–1304.

Zeger et al. (1992), "Globally optimal vector quantizer design by stochastic relaxation," *IEEE Transactions on Signal Processing*, 40(2):310–322.

Zeng et al. (1993), "A computerized autofluorescence and diffuse reflectance spectroanalyser system for *in vivo* skin studies," *Phys. Med. Biol.*, 38:231–240.

Zeng et al. (1997), "Optimization of fast block motion estimation algorithms," *IEEE Transactions on Circuits and Systems for Video Technology*, 7(6):833–844.

Zhang et al. (1999), "Shape from shading: a survey," *IEEE Transactions on Pattern Analysis and Machine Intelligence*, 21(8):690–706.

Zheng et al. (1991), "Estimation of illumination direction, albedo, and shape from shading," *IEEE Transactions on Pattern Analysis and Machine Intelligence*, 13(7):680–702.

Zhengfang et al. (1998), "Identification of Colonic Dysplasia and Neoplasia by Diffuse Reflectance Spectroscopy and Pattern Recognition Techniques," *Applied Spectroscopy*, 52(6):833–839.

\* cited by examiner

COLONIC POLYP DISCRIMINATION BY TISSUE FLUORESCENCE AND FIBEROPTIC PROBE

GOVERNMENT RIGHTS

This invention was made with government support under a Small Business Innovative Research Grant (Contract # 1R43CA75773-01) awarded by the Department of Health and Human Services. The government may have certain rights in the invention.

FIELD OF THE INVENTION

This invention relates generally to diagnosis of disease. More particularly, the invention relates to in situ diagnosis by optical methods.

BACKGROUND OF THE INVENTION

Polyps of the colon are very common. There are two major types of colonic polyps, neoplastic and non-neoplastic. Non-neoplastic polyps are entirely benign with no malignant potential and do not necessarily need to be resected. Hyperplastic polyps, juvenile polyps, mucosal prolapse and normal mucosal polyps are examples of non-neoplastic polyps. Conversely, neoplastic polyps are pre-malignant, a condition requiring resection and further surveillance. Examples of premalignant neoplastic polyps are tubular adenoma, villous adenoma and tubulovillous adenoma.

Conventional laser-induced fluorescence emission and reflectance spectroscopy can distinguish between neoplastic and non-neoplastic tissue with accuracies approaching about 85%. However, typically these methods require that the full spectrum be measured with algorithms dependent on many emission wavelengths.

SUMMARY OF THE INVENTION

This invention, in one embodiment, relates to an optical probe and methods for identifying neoplastic polyps of the colon during endoscopy or colonoscopy. In one embodiment, the probe comprises 6 collection fibers surrounding a single illumination fiber placed directly in contact with tissue. In one embodiment, a method of the invention comprises laser induced fluorescence using 337 nm excitation and a threshold classification model that depends on two fluorescence intensity ratios: the intensity at about 403 nm divided by the intensity at about 431 nm and the intensity at about 414 nm divided by the intensity at 431 nm. The invention enables determining whether a polyp is neoplastic. Of particular interest, the invention enables such determination at the time of endoscopy particularly for diminutive polyps. In a preferred embodiment, the invention provides for identification of polyps under about 10 mm in size. The invention provides methods that reliably distinguish between neoplastic and non-neoplastic polyps at the time of endoscopy or colonoscopy. As a result, patients with non-neoplastic polyps are not subjected to the risk and expense of polypectomy.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below. The drawings are not necessarily to scale, emphasis instead generally being placed upon illustrating the principles of the invention. In the drawings, like numerals are used to indicate like parts throughout the various views.

DETAILED DESCRIPTION

Instrument

Figure 1:
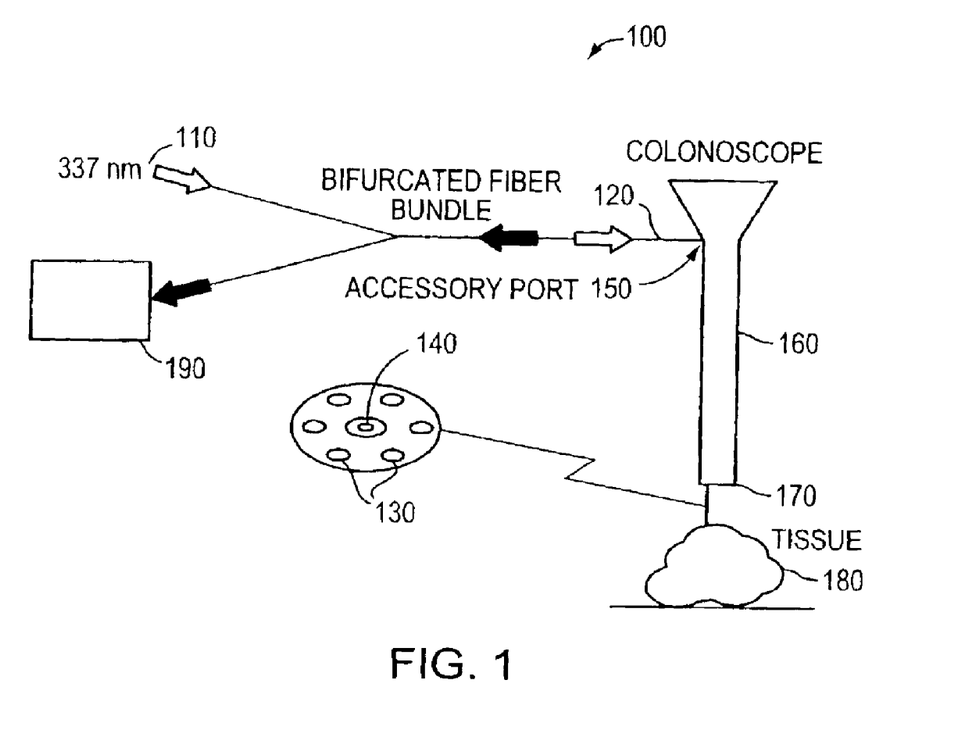
FIG. 1 is a schematic diagram showing an embodiment of the apparatus according to principles of the invention.

The invention in one embodiment involves delivering 337 nm excitation light to tissue via a single optical fiber and collecting remitted light with a plurality of optical fibers surrounding the illumination fiber. The apparatus 100 used in the embodiment is shown in FIG. 1. The apparatus 100 shown in FIG. 1 includes a source 110 of 337 nm illumination as the excitation. The excitation illumination is introduced into an optical fiber 120 for delivery to the tissue under examination. The illumination fiber 120 can be tapered starting at about 0.4 mm in diameter at the proximal end and ending at about 0.1 mm at its distal end. In the present embodiment, a plurality of optical fibers 130 are used to collect the response signal from the tissue under examination. In one embodiment, six collection fibers 130 are placed in an hexagonal array about the central optical fiber 120 that carries the excitation illumination. This geometry is termed herein the "six-around-one fiberoptic probe." The collection fibers are about 0.1 mm in diameter. The fiberoptic catheter 140 is delivered through the accessory port 150 of a typical endoscope 160 with the distal tip 170 gently touching tissue 180 to be examined. The returned light is separated into fluorescence bands at 403, 414 and 431 nm using a wavelength dispersive element 190 such as a spectrograph or dichroic filter system. The width of the bands should preferably be under 5 nm. The two intensity ratios ($I_{403}/I_{431}$ and $I_{414}/I_{431}$) are then formed and inputted in a linear discriminant analysis (LDA) threshold model to produce a score. The polyp is removed or left in place based on the sign of the score.

The invention involves illuminating a specimen, such as an in vivo specimen, using illumination having a first wavelength, and observing a response signal, such as a fluorescent response. The response signal is sampled at at least a second wavelength, a third wavelength, and a fourth wavelength. The intensity of the response signal at the second wavelength and at the third wavelength is normalized using the intensity at the fourth wavelength. The normalized responses are used at input values for a discrimination function analysis. The output of the discrimination function analysis is an indication that the specimen examined is healthy or is diseased.

Figure 2:
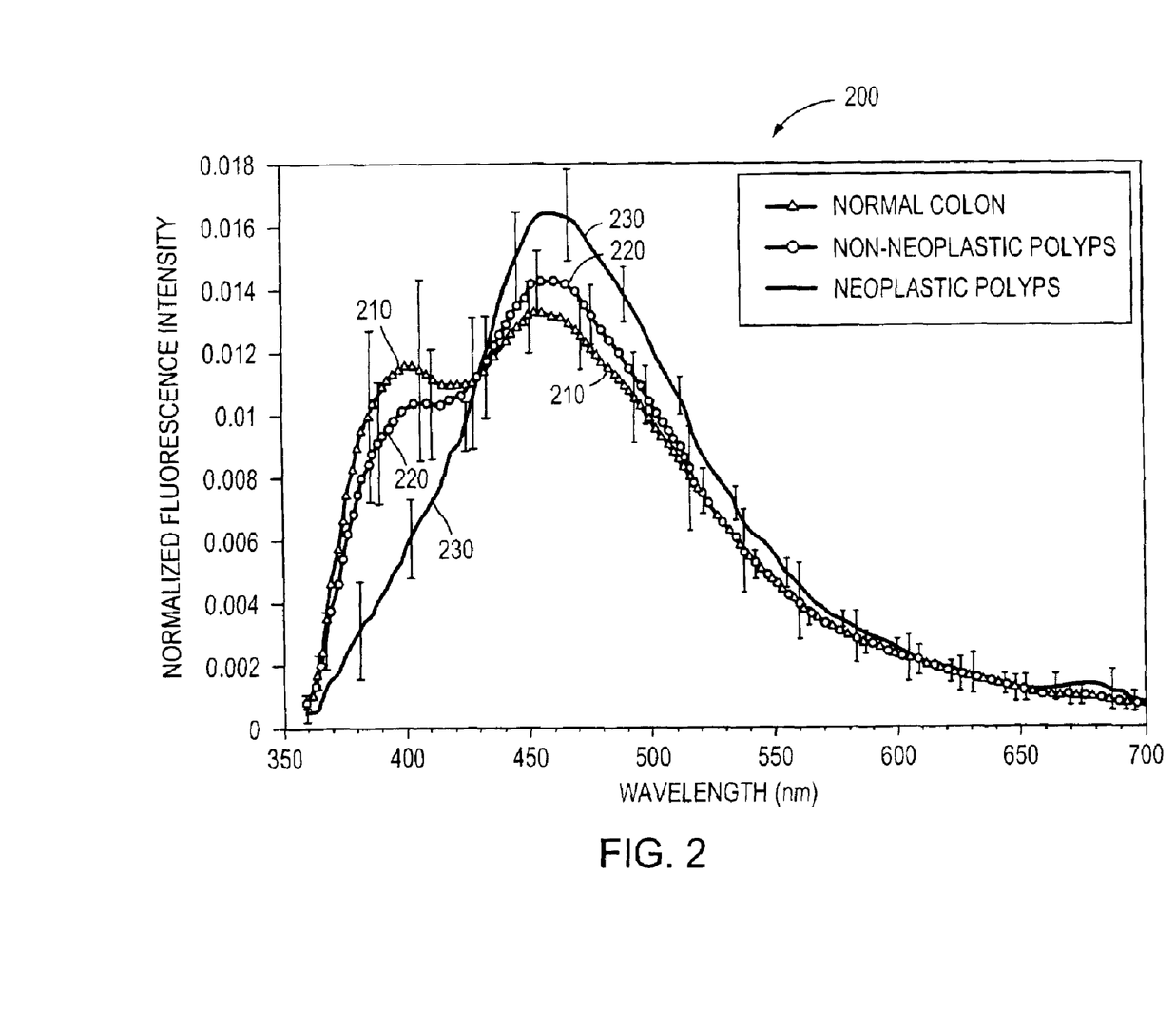
FIG. 2 is a plot of the normalized fluorescence spectra of normal colon, neoplastic polyps and non-neoplastic polyps, according to an embodiment of the invention.

Referring to FIG. 2, a plot 200 depicting a plurality of response spectra is shown, for different tissue types illuminated with the same 337 nm excitation illumination. The spectra observed correspond to tissues including normal colon 210, non-neoplastic polyps 220, and neoplastic polyps 230. The spectra 210, 220, 230 shown in FIG. 2 were recorded with the six-around-one fiberoptic probe.

Changes in optical properties of collagen and blood are the predominant factors in diagnostic differentiation among normal tissue, non-neoplastic polyps, and neoplastic polyps. An algorithm that treats collagen fluorescence, having a peak at about 403 nm in the system of the invention, and hemoglobin absorption, having a peak at about 414 nm for oxyhemoglobin, is sensitive to these changes.

Collagen and blood reside underneath the superficial cellular layer. A fiberoptic geometry designed to probe deeper into tissue but not too deep is more sensitive to changes in collagen and blood and hence in differentiating between polyps types. The six-around-one fiberoptic probe used according to principles of the invention probes deeper into tissue than does a single fiber system.

Interpatient variability in the intensity of fluorescent response is typically large and effects the diagnostic accuracy of techniques based on absolute fluorescence intensities. Historically, effective diagnostic algorithms have used some form of normalization to reduce interpatient variability. One common approach that has been used is to preprocess the data by normalizing the area under each fluorescence spectrum to unity. However, this approach requires that the entire fluorescence spectrum be measured to calculate the area to be used for the normalization factor. The necessity to record an entire spectral response simply to be able to obtain normalization data is redundant and inefficient. The inefficiency is particularly acute if only the emissions at 1 or 2 wavelengths are to be analyzed.

According to the invention, an intensity at a location such as at about 431 nm, between the fluorescence spectra of normal tissue, hyperplastic polyps and adenomatous polyps, is used as a normalization factor that provides effective normalization while requiring fluorescence to be measured at only one addition emission wavelength.

The combination of a new design of a fiberoptic probe for making measurements, an analytic method based on a small number of data points, and a simple method of obtaining a normalization factor for the data used provides enhanced diagnostic accuracy in distinguishing between neoplastic and non-neoplastic polyps. The efficacy of the new system and method is demonstrated in a single-center prospective clinical trial. A higher fraction of polyps were correctly classified with this technique, (e.g., accuracy=86%) when compared to other approaches. The accuracy of the method using two emission wavelengths is better than that obtained in retrospective clinical trials requiring many more wavelengths.

Analysis Method

Figure 3:
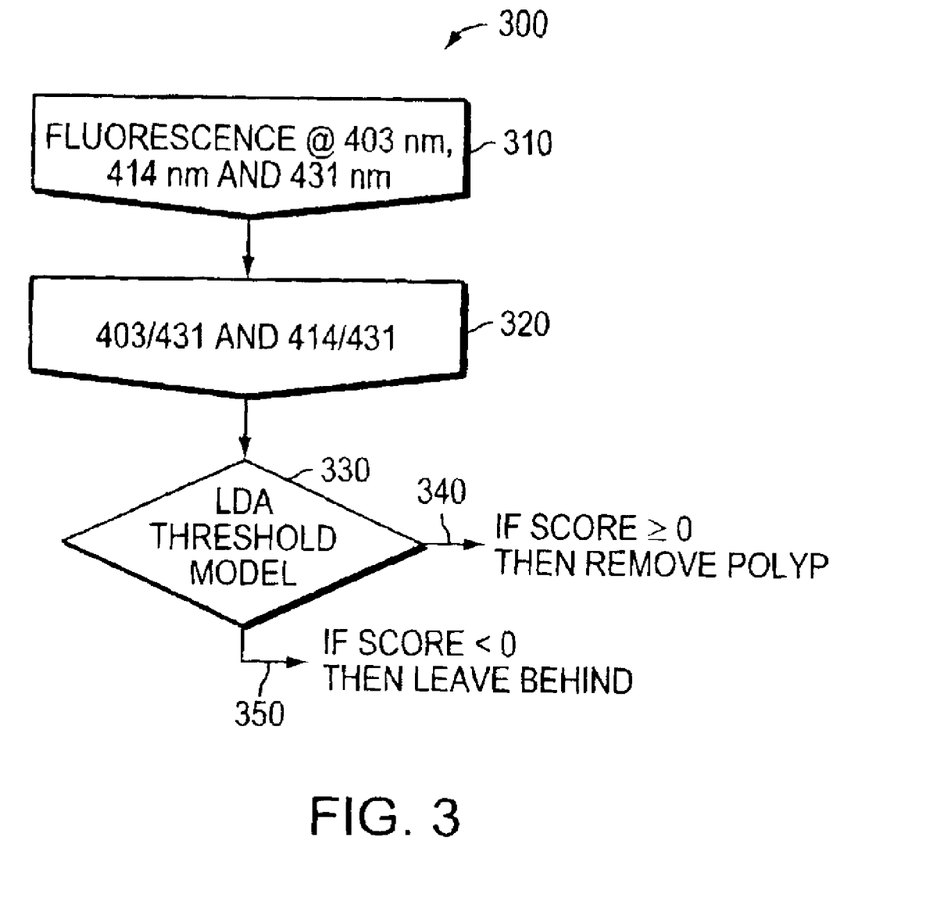
FIG. 3 is a flow diagram showing the steps of the analytical method according to principles of the invention.

FIG. 3 is a flow diagram 300 showing the steps of the analytical method. The method involves observing fluorescent intensities at about 403, about 414 and about 431 nm, as shown at step 310. The ratio of the intensity at about 403 nm to that at about 431 nm ($I_{403}/I_{431}$), and the ratio of the intensity at about 414 nm to that at about 431 nm ($I_{414}/I_{431}$) are formed, as indicated at step 320. The two ratios are then examined by comparison to a linear discrimination function, using linear discrimination analysis (LDA), as shown at step 330. A score value greater than zero is indicative of neoplasia, while a score value less than zero indicates non-neoplasia. Resection can be performed, or omitted, based on the score value that is obtained. Result 340 represents performing resection, while result 350 represents not performing resection.

Sensitivity Analysis

Figure 4:
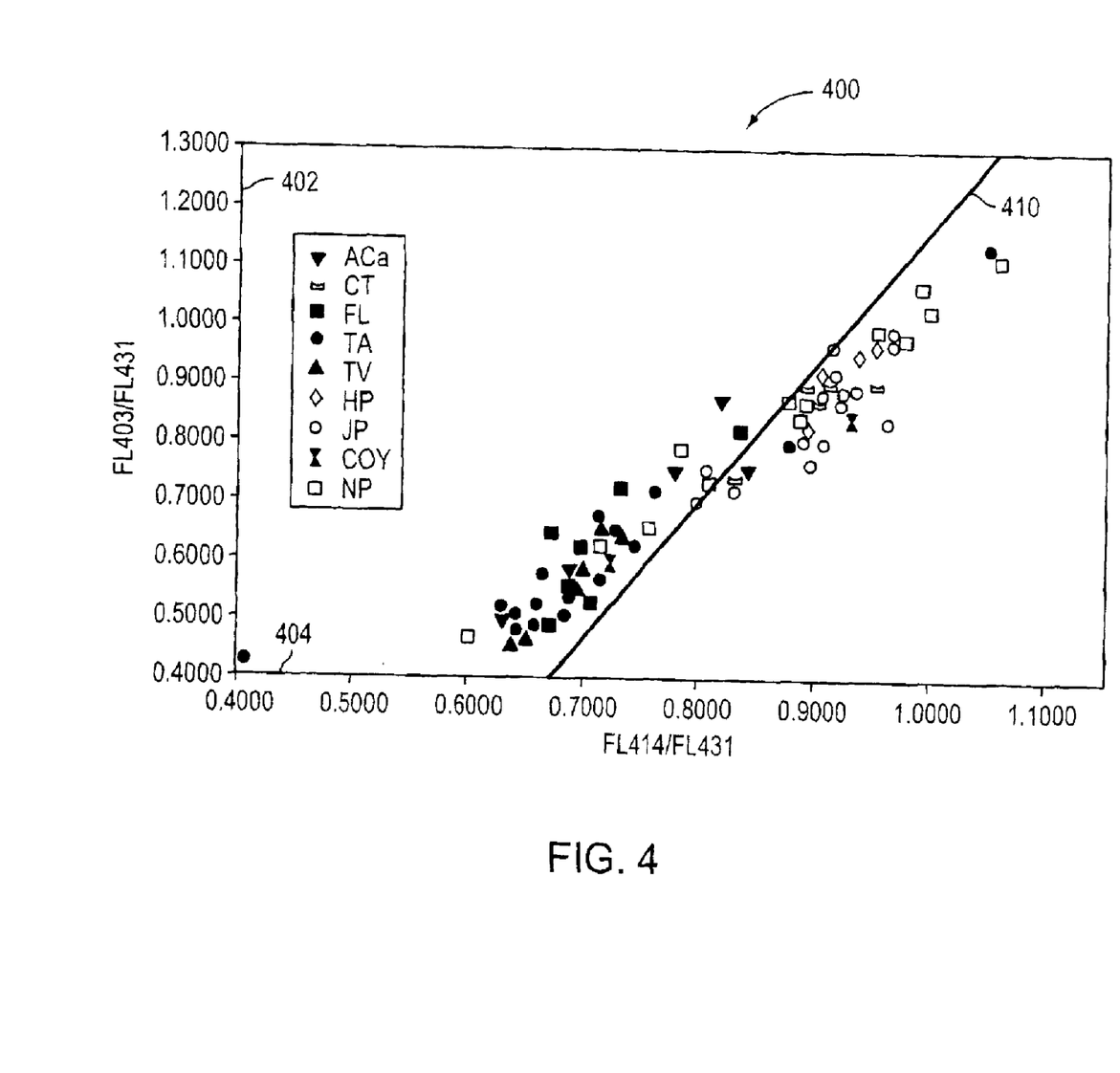
FIG. 4 is a graph showing polyp classification results obtained using a linear discriminant analysis according to principles of the invention.

FIG. 4 is a graph 400 showing polyp classification results obtained using a linear discriminant analysis. One hundred and fifty patients were enrolled in a prospective study in which 94 polyps were collected from 50 patients. In FIG. 4, the about 403 nm to about 431 nm fluorescence intensity ratio ($I_{403}/I_{431}$) was plotted along the vertical axis 402 against the about 414 nm to about 431 nm ratio ($I_{414}/I_{431}$) plotted along the horizontal axis 404 for a given polyp. The LDA threshold discrimination model is depicted as the line 410 in FIG. 4 where polyps corresponding to data points that lie above the line 410 are classified as neoplastic polyps and polyps corresponding to data points that lie below the line 410 are classified as non-neoplastic polyps. Using this model, 47 of 52 neoplastic polyps and 34 of 42 non-neoplastic polyps were classified correctly resulting in a sensitivity and specificity of 90% and 81%, respectively. In addition, 80 of 86 normal colonic tissue sites and 3 of 3 frank adenocarcinomas were correctly classified.

Potential Cost Savings

The ability to identify and distinguish benign and malignant polyps in situ could result in substantial cost savings. In this particular example, 39 of 94 polyps would have been spared from being resected and biopsied, representing a 41% savings in surgical and pathology charges. However, at present there is a false negative rate of 9.6%. The long term outcome of not resecting these polyps will need to be determined. In comparison, other techniques spared 14% of the polyps from being biopsied and had a false negative rate of 0.9%. If polyps greater than 5 mm in the latter study are excluded from this analysis, then 27% of the polyps would not have been biopsied and the technique would have a 3.2% false negative rate.

Application to Other Tissues

The system and method of the invention has been shown to work in colonic tissue. The invention, involving a new probe design and analytical method, can enhance the accuracy for identifying neoplasia in other tissues such as the esophagus, urinary bladder, oral cavity, bronchotracheal tree and cervix.

EQUIVALENTS

While the invention has been particularly shown and described with reference to specific preferred embodiments, it should be understood by those skilled in the art that various changes in form and detail may be made therein without departing from the spirit and scope of the invention.

What is claimed is:

1. A method of identifying a state of health of a tissue in vivo, the method comprising the steps of:

illuminating a tissue in vivo with light having a wavelength of about 337 nanometers;

receiving from the tissue a response comprising fluorescent light having wavelengths of about 403 nanometers, about 414 nanometers, and about 431 nanometers;

computing a first ratio, the first ratio being an intensity of the fluorescent light having a wavelength of about 403 nanometers divided by an intensity of the fluorescent light having a wavelength of about 431 nanometers;

computing a second ratio, the second ratio being an intensity of the fluorescent light having a wavelength of about 414 nanometers divided by the intensity of the fluorescent light having a wavelength of about 431 nanometers; and deducing a state of health of the tissue depending on the magnitude of the first ratio and the magnitude of the second ratio to a linear discrimination function.

2. The method of claim 1, wherein illuminating the tissue involves contacting the tissue with an illumination optical fiber.

3. The method of claim 1, wherein receiving from the tissue a response comprising fluorescent light involves contacting the tissue with a receiving optical fiber.

4. The method of claim 1, wherein the tissue in vivo comprises a polyp under about 10 millimeters in size.

5. The method of claim 1, wherein deducing a state of health of the tissue comprises deducing the state of health in real time.

6. A system for identifying a state of health of a tissue in vivo, comprising:

an illumination source for illuminating a tissue in vivo with light having a wavelength of about 337 nanometers, the source comprising an illuminating optical fiber;

a detector for receiving from the tissue a response comprising fluorescent light having wavelengths of about 403 nanometers, about 414 nanometers, and about 431 nanometers, the detection system comprising at least one optical fiber for receiving the fluorescent light;

a wavelength dispersive element for separating the fluorescent light into different wavelengths;

a computation system for computing a first ratio and a second ratio, the first ratio being an intensity of the fluorescent light having a wavelength of about 403 nanometers divided by an intensity of the fluorescent light having a wavelength of about 431 nanometers, the second ratio being an intensity of the fluorescent light having a wavelength of about 414 nanometers divided by the intensity of the fluorescent light having a wavelength of about 431 nanometers; and an analysis module for deducing a state of health of the tissue depending on the magnitude of the first ratio and the magnitude of the second ratio to a linear discrimination function.

7. The system of claim 6, wherein the illuminating optical fiber contacts the tissue.

8. The system of claim 6, wherein the at least one optical fiber for receiving the fluorescent light contacts the tissue.

9. The system of claim 6, wherein the tissue in vivo comprises a polyp under about 10 millimeters in size.

10. The system of claim 6, wherein the analysis module produces information about the state of health in real time.

* * * * *